United States Patent [19]

Lekieffre et al.

[11] Patent Number: 5,652,248
[45] Date of Patent: Jul. 29, 1997

[54] METHOD OF PREVENTING PERIPHERAL NEUROPATHIES INDUCED BY ANTICANCER AGENTS

[75] Inventors: Delphine Lekieffre, Paris; Jésus Benavides, Chatenay Malabry; Bernard Scatton, Villebon sur Yvette; Pascal George, Saint Arnoult en Yvelines, all of France

[73] Assignee: Synthelabo, Le Plessis Robinson, France

[21] Appl. No.: 327,589

[22] Filed: Oct. 24, 1994

[30] Foreign Application Priority Data

Jul. 29, 1994 [FR] France .................................. 94 09409

[51] Int. Cl.⁶ .................... A61K 31/445; A61K 31/335; A61K 31/44; A61K 33/24
[52] U.S. Cl. ..................... 514/317; 514/449; 514/283; 424/649
[58] Field of Search ..................... 514/317, 449, 514/283; 424/649

[56] References Cited

U.S. PATENT DOCUMENTS 4,690,931  9/1987  Wick et al. ............................ 514/317

OTHER PUBLICATIONS

Merck Index, 11th Ed., Merck & Co, Inc, Rahway, N.J., 1989, p. 1435.

Lipton et al, Neurology, vol. 39, pp. 368–373 (1989) Applicants should provide a copy of this reference.

*Primary Examiner*—Jerome D. Goldberg
*Attorney, Agent, or Firm*—Jacobson, Price, Holman & Stern, PLLC

[57] ABSTRACT

Eliprodil, or an enantiomer thereof, is indicated for combined administration with anticancer agents in order to prevent peripheral neuropathies induced by administration of the anticancer agents.

5 Claims, No Drawings

METHOD OF PREVENTING PERIPHERAL NEUROPATHIES INDUCED BY ANTICANCER AGENTS

The present invention relates to the use of eliprodil and enantiomers thereof for preparing medicines useful for preventing peripheral neuropathies induced by anticancer treatments. The invention also concerns pharmaceutical compositions comprising eliprodil or an enantiomer thereof and anticancer agents, and their use as an anticancer treatment not inducing peripheral neuropathies.

Eliprodil and its enantiomers can be used as the free base or a pharmaceutically acceptable acid addition salt.

Eliprodil [formula (I)]

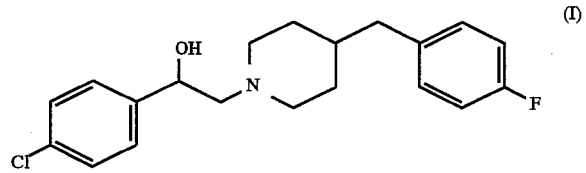

is a known compound. Its structure and neuroprotective properties are disclosed in U.S. Pat. No. 4,690,931.

Its enantiomers are described in French Utility Certificate FR 89 04835.

Further research has revealed the neurotrophic properties of eliprodil.

The purpose of these studies was to evaluate its possible use in the prevention of peripheral neuropathies induced by anticancer agents.

Some anticancer agents are indeed known to induce, at therapeutic doses, pathological alterations of sensory and motor peripheral nerve fibres, which limits their clinical use.

In this regard, paclitaxel (TAXOL®), a compound active in the treatment of malignant melanomas and ovarian carcinomas, is especially representative, for it induces sensory neuropathies which affect predominantly small diameter fibres (L. B. Lipton et al., Neurology, vol. 39, 368–373, 1989).

Paclitaxel is an alkaloid derivative which binds to tubuline, thus inducing microtubules aggregation. This disturbance, visible at the level of axons and Schwann cells, leads to axon degeneration and demyelinization.

A paclitaxel neuropathy, reproducing the human pathology, can easily be induced in animals. This animal model makes it possible to assess the effectiveness of pharmacological agents towards the peripheral neuropathies induced by various chemotherapies.

The assessment of the preventive effects of eliprodil on neuropathies induced by paclitaxel was carried out as follows:

Paclitaxel was administered intraperitoneally at the dose of 20 mg/kg, for 6 consecutive days, to $OF_1$ (Iffa Credo) mice, weighing 10 to 12 g. It was injected as a suspension in a 10% solution of Cremophor® EL in a volume of 0.1 ml/10 g of body weight.

Eliprodil hydrochloride was prepared as a suspension in a 0.1% Tween 80 aqueous solution and administered intraperitoneally, twice a day for 8 days, at the dose of 1 mg/kg, the first injection beginning 24 hours before that of paclitaxel.

The animals were divided into 4 experimental groups:
absolute controls receiving neither paclitaxel nor eliprodil,
treated controls receiving eliprodil only,
animals treated with paclitaxel only,
animals treated with paclitaxel and eliprodil.

Five days after the last injection of paclitaxel, the animals were subjected to a test to evaluate their sensitivity to pain ("Tail-flick" test). In this test, the end of the mouse tail (2 mm) is set between a light beam (100 watts) and a photocell, coupled to an automatic counter. The time after which the animal removes its tail from the light beam (latency) is recorded, an increase in latency being a good index of sensory disturbances (see S. C. Apfel, R. B. Lipton, J. C. Arezzo, J. A. Kessler, in Ann. Neurol., 29, No. 1, 87–90, 1991).

The following results were obtained:
control mice showed a latency of 3 seconds, which was not modified by the treatment with eliprodil,
in the paclitaxel treated group, the latency was increased by 45%,
in the group treated with paclitaxel+eliprodil, the latency was the same as in the control groups.

These results show that the treatment combining eliprodil with paclitaxel totally counteracts the sensory disturbances induced by paclitaxel.

It appears that eliprodil prevents the sensorial disturbances associated with the administration of paclitaxel. Eliprodil and its enantiomers can therefore be used for preparing medicines for preventing neuropathies induced by paclitaxel or any other neuropathy-inducing anticancer agent, such as cisplatin, vinblastine, vincristine or vindesine.

Eliprodil and its enantiomers can be used in association with suitable excipients, in any galenic form appropriate for oral, parenteral or local administration, for example in the form of tablets, capsules, solutions or transdermal patches, containing 0.1 to 100 mg of active principle per unit dose.

They can be administered prior to and/or simultaneously with and/or after the anticancer agent, at the rate of 1 to 3 unit doses per day.

They can also be administered as pharmaceutical compositions, comprising eliprodil or an enantiomer thereof and an anticancer agent, in association with suitable excipients, in any galenic form as mentioned above.

These compositions contain 0.1 to 100 mg of eliprodil or an enantiomer thereof, and are administered according to the mode of administration prescribed for the anticancer agent.

We claim:

1. A method of preventing peripheral neuropathies induced by anticancer in a patient in need thereof, which comprises administering to the patient a therapeutically effective amount of eliprodil or an enantiomer thereof, prior to and/or simultaneously with and/or after the administration of an anticancer agent selected from the group consisting of paclitaxel, cisplatin, vinblastine, vincristine, and vindesine.

2. A method of preventing peripheral neuropathies induced by anticancer agents in a patient in need thereof, which comprises administering to the patient a therapeutically effective amount of a pharmaceutical composition comprising eliprodil or an enantiomer thereof and a therapeutically effective amount of a peripheral-neuropathy-inducing anticancer agent selected from the group consisting of paclitaxel, cisplatin, vinblastine, vincristine, and vindesine.

3. A pharmaceutical composition comprising a therapeutically effective amount of eliprodil or an enantiomer thereof and a therapeutically effective amount of a peripheral-neuropathy-inducing anticancer agent selected from the group consisting of paclitaxel, cisplatin, vinblastine, vincristine, and vindesine together with pharmaceutically acceptable excipients.

4. A pharmaceutical composition according to claim 3 wherein the amount of eliprodil or an enantiomer thereof is 0.1 to 100 mg.

5. A pharmaceutical composition comprising a therapeutically effective amount of eliprodil or an enantiomer thereof and a therapeutically effective mount of a peripheral-neuropathy-inducing anticancer agent together with pharmaceutically acceptable excipients, wherein the anticancer agent is paclitaxel.

* * * * *